United States Patent [19]
Heath

[11] Patent Number: 6,060,648
[45] Date of Patent: May 9, 2000

[54] SEEDLESS TOMATOES AND METHOD FOR MAKING THE SAME

[75] Inventor: Douglas Heath, Rocklin, Calif.

[73] Assignee: Seminis Vegetable Seeds, Inc., Saticoy, Calif.

[21] Appl. No.: 08/957,867

[22] Filed: Oct. 27, 1997

[51] Int. Cl.⁷ .............................. A01H 5/00; A01H 5/08; A01H 1/04

[52] U.S. Cl. ................ 800/317.4; 800/271; 800/274

[58] Field of Search .................. 800/200, DIG. 4, 800/260, 271, 274, 298, 317.4

[56] References Cited

U.S. PATENT DOCUMENTS 4,009,020  2/1977  Starke et al. ................................ 71/76

FOREIGN PATENT DOCUMENTS 0363819  10/1989  European Pat. Off. .......... A01H 1/02

OTHER PUBLICATIONS

T.C. Tigchelaar. Tomato breeding in Breeding Vegetable Crops, ed. by M.J. Bassett, AVI Publishing Company, Inc., Westport, Connecticut, 1986.
Diaz et al. Effects of parthenocarpy on fruit quality in tomato. J. Amer. Soc. Hort. Sci. 112(4):634–637, 1987.
Baggett, J.R. et al., *HortScience.* 13(5):599. (1978).
Baggett, J.R., et al., *HortScience.* 21(5):1245–1247. (1986).
Baggett, J. R., et al., *HortScience.* 30(3):649–650. (1995).
Baggett, J.R. et al., *HortScience.* 17(6):984–985. (1982).
Baggett, J. R. et al., *HortScience.* 13(5):598. (1978).
Baggett, J. R., et al., *HortScienc.* 20(5):957–958. (1985).
Costa, Joaquin, et al., *HortScience.* 27(2):185–186. (1992).
Diez, M., et al., Proceeding of the XIth Eucarpia Meetings on Tomato Genetics and Breeding [edited by Cuartero, J., Gomez–Guillamon, M.L., Fernandez, Munoz, R.J.] 137–141. (1990).
Georgiev, H. et al., Proceedings of the XIth Eucarpia Meetings on Tomato Genetics and Breeding [edited by Cuartero, J., Gomez–Guillamon, M.L., Fernandez–Munoz, R.] 153–155. (1990).
Herrington, M.E., et al., *HortScience.* 20(5):958–959. (1985).
Lipari, V., et al., *Acta Horticulturac.* 366:79–84. (1994).
Lukyanenko, A. N., Monograms on Theorectical and Applied Genetics 14. Genetic Improvement of Tomato[edited by Prof. Kalloo] 167–177. (1991).
Melchers, Georg, et al., *Proc. Natl. Acad. Sci.* USA 89:6832–6836. (1992).
Natural parthenocarpy in tomato. IV. A study of the polygenic control of parthenocarpy in line 75/79. Argonomie.9:63. (1989).
Romano, D. et al., *Acta Hotticulturac.* 366:57–63. (1994).
Rylski, Irene, et al., *Acta Horticulturac.* 366:45–55. (1994).
Splittstoesser, W., Proceeding of the Plant Growth Regular Society of America [edited by Cooke, A.R.] 206–211. (1988).
Stevens, Allen, M., et al., Genetic and Breeding The Tomato Crop, A Scientific Basis for Improvement [edited by J. Atherton and J. Rudich Chapman and Hall London] 79–80. (1986).
Barg, R., et al., Differential Regulation of a fruit specific 62 kDa protein in developing Parthenocarpic (pat–2/pat–2) and Seeded Tomato Fruits Proceedings of the XIth Eucarpia Meeting on Tomato Genetics and Breeding [edited by Cuartero, J.; Gomez–Guillamon, M.L.; Fernandez–Munoz, R.] 143. (1990).
Lin, Steve et al., *The Journal of Heredity.*, 75:62–66, (1984).
Mazzucato, Andrea et al., Development., 25:107–115, (1998).
Chareonboonsit et al., Hortscience vol. 19(5):633 (1984).

*Primary Examiner*—Lynette R. F. Smith
*Assistant Examiner*—Melissa L. Kimball
*Attorney, Agent, or Firm*—Rockey, Milnamow & Katz, Ltd

[57] ABSTRACT

The present invention involves tomatoes which are substantially seedless. The tomatoes of the present invention are made by crossing a tomato plant containing at least one parthenocarpic gene as the male parent with a male sterile tomato plant containing at least one parthenocarpic gene as the female parent. The tomatoes resulting from this cross are substantially seedless.

5 Claims, 1 Drawing Sheet

(1 of 1 Drawing Sheet(s) Filed in Color)

FIGURE 1A                    FIGURE 1B

SEEDLESS TOMATOES AND METHOD FOR MAKING THE SAME

TECHNICAL FIELD OF THE INVENTION

The present invention involves seedless tomatoes and a method of producing said tomatoes.

BACKGROUND OF THE INVENTION

Many crops set fruit within a particular range of temperatures and under certain environmental conditions. Beyond this range of temperatures and environmental conditions, fruit typically does not set because of the lack of production of sufficient amounts of fertile pollen and difficulties in pollination and fertilization. For example, tomatoes set fruit in a narrow range of temperatures of 15° to 21° C. (night) and 30° to 35° C. (day). A. N. Lukyanenko, "Parthenocarpy in Tomato," *Monographs on Theoretical and Applied Genetics* 14, pgs. 167–177 (1991).

Parthenocarpy is the production of fruit without fertilization. Certain environmental conditions favor parthenocarpy such as high or low temperatures day or night, low light intensity, and high humidity. Parthenocarpy may be induced artificially or may occur naturally. In induced parthenocarpy, various growth regulators can be used to facilitate fruit setting. For example, auxins are commonly applied to facilitate fruit setting in tomato (*Lycopersicon esculentum*) grown during winter-spring on the Mediterranean coast.

Natural or genetic parthenocarpy may be obligate or facultative. Obligative parthenocarpy results from genetic sterility, arises without any external stimulation, and requires a vegetative method of propagation. Obligative parthenocarpy is found in such fruits as the banana and pineapples A. N. Lukyanenko, "Parthenocarpy in Tomato," *Monographs on Theoretical and Applied Genetics* 14, pgs. 167–177 (1991). Facultative parthenocarpy is found in tomato and other species in which the processes of pollination and fertilization depend on narrow environmental limits. Id. In facultative parthenocarpy, seeded or seedless fruits are produced in response to environmental stimuli. Id. For example, the parthenocarpic tomato line "Severianin" from the Gribovskja Experimental Vegetable Station near Moscow, Russia, was found to have the remarkable ability to produce seedless or seeded fruits of similar weight depending on the environmental conditions. Splittstoesser, Walter E., "Temperature influences Parthenocarpic Fruit Production in Tomato", Proc. Plant Growth Regal. Soc. Am (1988). It is also known that naturally occuring parthenocarpic lines have a greater amount of growth-promoting substances in the ovary and as a result, the failure of pollination or lack of seed formation will not prevent the development of fruit.

Many cultivars exhibiting parthenocarpy from around the world have been studied, thus, various sources of parthenocarpy are known. Parthenocarpy is known to be controlled genetically by one or more recessive genes. Many recessive genes controlling parthenocarpy are known. These genes are pat, pat-2, pat-3, pat-4, and pat-5. A short anther (sha) allele has also been found to produce parthenocarpic fruits. A seed development suppressor (sds) allele has also been found which produces normal fruit without seeds or only with a little quantity of very small seeds.

One of the problems with parthenocarpic fruit is that their quality tends to be questionable. For example, parthenocarpic fruit tends to be smaller in size than normal fruit. Also, acidity tends to be lower in parthenocarpic fruit, which has an adverse effect on flavor. Additionally, parthenocarpic fruit, especially tomatoes, frequently suffer from various malformations such as puffiness when produced under low temperature conditions.

The cultivated tomato, *Lycopersicon esculentum*, is one of the most important vegetable crops in the United States and worldwide, with several million tons being produced each year in the United States alone. The commercial importance of the crop has necessitated a constant effort to improve cultivated varieties.

Several parthenocarpic seedless tomatoes are known. For example, 30% of the tomatoes from the tomato line "Farthest North" have no seed. (Baggett, J. R., et al., *Hortsci.* 13(5):598 (October 1978); Baggett, J. R., et al., *Hortsci.* 13(5):599 (October 1978). Approximately 50–70% of the tomatoes from the tomato lines Oregon 11 and Gold Nugget have no seed. (Baggett, J. R., et al., Hortiscience, Alexandria American Society for Horticultural Science 17(6), 984–985 (December 1982). Baggett, J. R., et al., Hortiscience, Alexandria, Va.: American Society for Horticultural Science, 20(5), 957–958 (October 1985)). Furthermore, one of the problems with these seedless tomatoes is that no one can determine if the tomato is seedless without first cutting into the tomato. Therefore, prior approaches for obtaining seedless tomatoes have yielded a certain percentage of fruit that do not contain seeds. This is not a practical or commercially beneficial approach for obtaining seedless fruit.

A substantially seedless tomato is not presently commercially available. A need for such a tomato exists, in particular, such a tomato of good quality especially for individuals on strict dietary restrictions who cannot eat food products containing seeds. For example, individuals recovering from surgery to repair a ruptured portion of their gastrointestinal tract typically cannot eat foods that contain seeds. The problem is that these seeds may become trapped in the sutures in the repaired area of the gastrointestinal tract and thereby impair the healing process. If the wall of the gastrointestinal tract does not adequately heal, a further rupture could occur.

Moreover, substantially seedless tomatoes would be beneficial in the food preparation and process products industries. For example, completely seedless tomatoes would make the preparation of certain products such as tomato sauce and tomato paste more efficient and less costly because the seeds would not need to be removed prior to processing.

Therefore, one object of the present invention is to provide a substantially seedless parthenocarpic tomato that exhibits good quality. A second object of the present invention is to provide a method for producing said seedless tomatoes.

SUMMARY OF THE INVENTION

The present invention involves tomatoes (*Lycopersicon esculentum*) that are substantially seedless. The tomatoes of the present invention are about 100% seedless. The seedless tomatoes of the present invention are made by crossing a tomato plant (*Lycopersicon esculentum*) containing at least one parthenocarpic gene as the male parent with a male sterile tomato plant (*Lycopersicon esculentum*) containing at least one parthenocarpic gene as the female parent. The male and female parental lines may contain any parthenocarpic gene such as pat, pat-2, pat-3, pat-4, and pat-5, sha, and sds. The parthenocarpic gene(s) in the male and female parental lines should be identical in order to insure the production of the seedless tomatoes of the present invention.

The seedless tomatoes of the present invention retain the size of fruit of the parent lines, and therefore a means is provided for obtaining seedless tomatoes of commercially acceptable size. The seedless tomatoes of the present invention also have good flavor (sugar and acid balance) and do not exhibit any malformations such as puffiness.

DESCRIPTION OF THE DRAWINGS

The file of this patent contains at least one color photograph. Copies of this patent with the color photographs will be provided by the Patent and Trademark Office upon request and payment of the necessary fee.

FIG. 1A is a tomato half from a normal seeded tomato. FIG. 1B is a tomato half of the seedless tomato of the present invention.

DETAILED DESCRIPTION OF THE DRAWINGS

Figure 1:
FIG. 1 is a color photograph of cut halves from two different tomatoes.

The present invention involves seedless tomatoes (*Lycopersicon esculentum*) and a method of producing seedless tomatoes. As used herein, the term "seedless tomato" refers to a tomato that does not contain any fertilized mature seeds. While the tomatoes of the present invention do not contain any fertilized mature seeds, the tomatoes may contain unfertilized ovaries, which are small and white in color. These unfertilized ovaries are not considered to be true seeds.

The seedless tomatoes of the present invention are substantially seedless. As used herein, the term "substantially seedless" means that the tomato is at least 90% seedless. Preferably, the seedless tomatoes of the present invention are about 95% to about 99% seedless, most preferably, the tomatoes of the present invention are about 100% seedless.

The seedless tomatoes of the present invention are prepared by crossing a tomato plant (*Lycopersicon esculentum*) containing at least one parthenocarpic gene as the male parent with a male sterile tomato plant (*Lycopersicon esculentum*) containing at least one parthenocarpic gene as the female parent. The male and female plants crossed to produce the seedless tomatoes of the present invention should each be homozygous for the parthenocarpic gene(s) and contain identical parthenocarpic genes.

The male and female parental lines employed to produce the seedless tomatoes of the present invention must contain at least one parthenocarpic gene. The parental lines may contain any parthenocarpic gene such as pat, pat-2, pat-3, pat-4, pat-5, sha, sds, etc. In order to insure the production of substantially seedless tomatoes, the male and female parental lines used in the hybridization should preferably contain the identical parthenocarpic genes. For example, if the male parental line contains the pat gene, the female parental line should also contain the pat gene.

Many tomato lines containing parthenocarpic genes are publicly available for use as the male parental line in the method of this invention. Examples of tomato lines that contain parthenocarpic genes that can be used in this invention are listed in the table below.

| Cultivar/ Breeding line | Country of origin | Genetic Control | Reference |
|---|---|---|---|
| Severianin | USSR | pat-2 | Philouze et al., Genotype-and-environment-in-breeding-greenhouse-tomatoes, 2, 54–64 (1978), herein incorporated by reference. |
| Sub Arctic Plenty | Canada | pat-5 | Nuez et al., J. Plant Breeding 96(3) 200–206 (April 1986), herein incorporated by reference. |
| Oregon Cherry | U.S.A. | unknown | Baggett et al., Hort Science 13(5): 598 (1978), herein incorporated by reference. |
| Oregon T5-4 | U.S.A. | unknown | Baggett et al., Hort Science 13(5): 598 (1978), herein incorporated by reference. |
| Gold Nuggett | U.S.A. | unknown | Baggett et al., Hort Science 20(5): 957–958 (1985), herein incorporated by reference. |
| Santiam | U.S.A. | unknown | Baggett et al., Hort Science 21(5): 1245–1247 (1986), herein incorporated by reference. |
| Oregon-11 | U.S.A. | unknown | Baggett et al., Hort Science 17(6): 984–985 (1982), herein incorporated by reference. |
| Siletz | U.S.A. | unknown | Baggettet al., Hort Science 17(6): 984–985 (1982), herein incorporated by reference. |
| Oregon Spring | U.S.A. | unknown | Baggett et al., Hort Science 21(5): 1245–1247 (1986), herein incorporated by reference. |
| Oregon Star | U.S.A. | pat-2 | Baggett et al., Hort Science 30(3): 649 (1995), herein incorporated by reference. |
| Oregon Pride | U.S.A. | pat-2 | Baggett et al., Hort Science 30(3): 649 (1995), herein incorporated by reference. |

Oregon-11, Gold Nuggett, Oregon Spring, Oregon Star, Oregon Pride and Siletz are commercially available from Territorial Seed Co., P.O. Box 157, Cottage Grove, Oreg. 97424. Gold Nuggett and Oregon Spring are also available from Johnny's Selected Seeds, Foss Hill Road, Albion, Me. 04910-9731 and Nichol's Garden Nursery, 1190 North Pacific Highway, Albany, Oreg. 97321. Santiam and Oregon Star are also commercially available from Nichol's Garden Nursery in Albany, Oreg.

In addition, parthenocarpic genes from homozygous tomato lines may be transferred to tomato lines having commercially desirable characteristics by backcrossing. The homozygous tomato line containing the parthenocarpic genes is used as the donor parent and the tomato line having commercially desirable characteristics is used as the recurrent parent. After the initial cross of the recurrent parent with the donor parent, the resulting $F_1$ progeny is self-pollinated. The $F_2$ progeny are then grown out and only those progeny which have seedless fruits combined with the maximum desirable horticultural traits are selected. These selections are then either selfed down further to fix desirable horticultural traits while retaining the parthenocarpic gene, or further backcrossing with the recurrent parent is employed until satisfactory $F_2$ segregates are recovered. The tomato line may now be used as the male parental line in the crossings of the present invention.

The female parental line used to make the seedless tomatoes of the present invention contains at least one parthenocarpic gene and also exhibits male sterility. The parental line may be cytoplasmically or genetically male sterile. As used herein, a plant is "male sterile" if it either produces no pollen or non-viable pollen. Self-fertilization is eliminated in male sterile plants. Male sterile plants allow a breeder to produce hybrid seed more economically by controlling cross-fertilization in the flower of a plant. Cross-fertilization can be controlled by preventing the female parent front self-fertilizing. Once rendered male sterile, the plant may then be hybridized with a gene donor plant possessing the desired characteristics. In this invention, the male sterile female tomato plant is hybridized with a male fertile male tomato plant that contains at least one identical parthenocarpic gene pair.

One way to effectuate male sterility is through the use of cytoplasmic male sterility. Present belief is that genetic factors controlling cytoplasmic male sterility (CMS) are found in the cytoplasm, particularly in the series of the mitochondrial DNA. Two common cytoplasmic male sterilities in plants are Ogura male sterile cytoplasm of *Raphanus sativus* and polima male sterile cytoplasm of *Brassicas napus*. Other cytoplasmic male sterilities and methods for making said sterility are also well known in the art and available for use in this invention. For example, European patent application 363.819 A1 describes a method of producing male-sterile tomato plants by fusing tomato protoplasts that contain inactivated cytoplasmic elements with Solanum protoplasts that contain inactivated nuclear elements to obtain fusion products that can be regenerated into male sterile tomato plants.

In tomatoes, cytoplasmic male sterility can be transmitted by crossing. The female (egg) parent contributes the cytoplasm, therefore, crossing to CMS females produces CMS progeny. The nuclear genes, however, are heterozygous. Therefore, six to eight generations of backcrossing are required to produce a CMS breeding line that is homozygous for horticulturally desirable nuclear characters.

Alternatively, cytoplasmic male sterile tomato lines can be produced by protoplast fusion. For example, a protoplast from a plant having commercially desirable traits may be fused with a protoplast from a CMS line to produce male sterile plants.

Generally, protoplasts for fusion may be obtained by conventional enzymatic techniques. The enzymatic isolation of protoplasts can be performed using a two-step (or sequential) or a one-step method. In the two-step method, plant tissue is first treated with a macerozyme or pectinase which separates the cells by degrading the middle lamella. The freed cells are then treated with cellulase, which releases the protoplasts. In general, the cells are exposed to the different enzymes for shorter periods than are used in the one-step method. In the one-step method, the tissue is subjected to a mixture of enzymes, including macerozyme and cellulase.

Because protoplasts are negatively charged, they will not spontaneously fuse. Therefore, fusion of the protoplasts must be induced. Fusion of the protoplasts can be induced chemically, by treating the protoplasts with high levels of calcium at a high pH, or by employing polyethylene glycol. Additionally, electrical methods can also be used to induce protoplast fusion, such as the electric field pulse technique disclosed by Vienken et al. *Physiol. Plant* 53:64 (1981), herein incorporated by reference.

Prior to the fusion, the nuclear material of one of the protoplasts, such as a protoplast from the CMS line, is either removed or inactivated in order to insure that the protoplast donates only the cytoplasm. The inactivation of the nuclear material can be accomplished by irradiation using gamma, UV, or X-rays. In some instances, the genetic material in the cytoplasm is inactivated prior to fusion so that the protoplast only donates the nuclear material. The inactivation of the cytoplasmic material can be accomplished chemically, by exposing the protoplasts to a compound, such as iodoacetic acid or Rhodamine 6-G. Generally, these compounds block the replication or disrupt the mitochondrial DNA.

Once the protoplasts are fused, they are cultivated in an appropriate culture medium comprising a well-balanced nutrient supply for protoplast growth and calli formation. The medium contains micro- and macro-elements, vitamins, amino acids and small amounts of carbohydrates, e.g., various sugars such as glucose. The culture medium also comprises plant hormones (auxins and cytokines) which are able to regulate cell division and shoot regeneration. Cytoplasmically male sterile plants are then regenerated.

Any male sterile tomato plant can be used in this invention. For example, cytoplasmically male sterile tomato plants produced according to the method described in European patent, 363 819 A1, herein incorporated by reference, can be used in this invention.

The male sterile tomato plants used as the female parental line must also contain at least one parthenocarpic gene which is identical to the parthenocarpic gene contained in the male parental line. The female parental line may be prepared by backcrossing tomato lines homozygous for at least one of the parthenocarpic genes with the male sterile tomato plants. This backcrossing strategy differs from male inbred development in that it involves straight backcrossing of the parthenocarpic inbred to the CMS female since no self-pollination is possible, the horticulturally acceptable parthenocarpic line acts as the maintainer of the CMS female line. The backcrossing is continued until the CMS tomato line is homozygous for the parthenocarpic gene. Homozygosity is achieved once 100% of the plant population sets parthenocarpic fruit.

The seedless tomatoes of the present invention are obtained by hybridization of the male parental line with the female parental line. The resulting progeny are about 90% seedless preferably about 95% to about 99% seedless and most preferably 100% seedless. It should be noted, however, that if a pollinator such as a bee, pollinates the female parental line with pollen from a fertile line that does not contain at least one identical parthenocarpic gene as in the female parental line, then the progeny will not be about 90% seedless.

The present invention also relates to a method of making a hybrid *Lycopersicon esculentum*, the method comprising the steps of crossing a *Lycopersicon esculentum* plant containing at least one parthenocarpic gene as the male parent with a cytoplasmically male sterile *Lycopersicon esculentum* plant containing at least one parthenocarpic gene as the female parent produce a *Lycopersicon esculentum*. The hybrid plant provides a fruit (*Lycopersicon esculentum*) that is male sterile. For optimum fruit set, the hybrid plants should be grown under a photoperiod of thirteen (13) hours or greater.

Generally, when cytoplasmic male sterility is employed in plants, a restorer gene must be transferred from the male pollinator in order to ensure adequate fertility in the $F_1$ offspring. More specifically, the function of the restorer gene is to restore fertility in the hybrid thereby allowing for fruit set. By using a parthenocarpic gene in the male parent, cytoplasmic male sterile *Lycopersicon esculentum* hybrids can be made that do not require a restorer gene from the male parent. A restorer gene is not required because the parthenocarpic gene expands the ovary, making fruit even though the fruit does not contain any seeds.

Some varieties of seedless tomatoes of the present invention have locules that do not increase in size during the development of the tomato at the same rate as conventional tomatoes. Because the locules in these tomatoes remain smaller, there is larger surface area of septal fused carpels than in conventional tomatoes. FIG. 1 shows a black and white photograph of halves from two different tomatoes. FIG. 1A shows a tomato half from a normal seeded commercial tomato. FIG. 1B shows a tomato half from a seedless tomato produced by the method of the present invention. As can be seen in these photographs, the tomato half in FIG. 1B has more flesh than the tomato half in FIG. 1A. Therefore, the seedless tomatoes of the present invention often contain more flesh than conventional tomatoes.

Additionally, the seedless tomatoes of the present invention exhibit a good sugar and acid balance which provided the tomato with a good flavor. Also, the seedless tomatoes of the present invention exhibit a higher sugar content than most conventional tomatoes.

The elevated sugar levels of the present invention are believed to relate to the fact that there are no seeds acting as a "sink", which normally assimilates free sugars present in the gel. The term "sink" is used in connection with plants to refer to a part of a plant that preferentially receives more photosynthate (sucrose) than other plant parts. Seeds constitute the dominate "sink" on plants because they represent the next generation or offspring of the plant. Plants that bear seeds contain a genetic makeup that codes for preferential translocation of sucrose to developing seeds, particularly under stress. With the parthenocarpic tomatoes of the present invention, it appears that the unfertilized, small ovules are not able to absorb the sugars translocated into the ovary, thus resulting in free sugars left for the enjoyment of the consumer.

The seedless tomatoes of the present invention do not exhibit any malformations, such as puffiness and exhibit a commercially acceptable size.

Finally, the seedless tomato of the present invention slice better than conventional tomatoes, due to the smaller locular gel areas.

By way of example and not limitation, examples of the present invention will now be given.

Example 1

Description of a Method for Preparing Seedless Tomato 96 FH 241

This example describes the development of the seedless tomato 96 FH 241 according to the method of the present invention.

96 FH 241 was developed as follows. A cytoplasmically male sterile (CMS) tomato plant called "CMS VFN8" was crossed as the female parent with a tomato plant called "Det. Parth 1" using traditional cross hybridization techniques. CMS VFN8 is a proprietary cytoplasmically male sterile tomato plant obtained from Tokita Seed Co., Ltd, Tokyo, Japan. Seeds of the hybrid parent VFN8, a Petoseed inbred line with resistance to *Verticillium dahliae* race 1, *Fusarium oxysporum* race 1, and the root knot nematode *Meloidogyne incognita*, were used as the nuclear donor parent in a protoplast fusion experiment wherein the mitochondria of cytoplasmically-male sterile *Solanum acaule* was substituted for the mitochondria of male-fertile *Lycopersicon esculentum*, "VFN8. The plant type of VFN8 is a vigorous determinate, and fruit size is large-extra large (200–250 grams), with good flavor.

Det. Parth 1 is a determinate parthenocarpic tomato plant which is a proprietary inbred line of Seminis Vegetable Seeds, Inc., the assignee of the present invention. Det. Parth 1 contains the pat-2 parthenocarpic gene. Det. Parth 1 is a determinate bush tomato with large-extra large (200–250 gram) fruit. The fruit have green-shoulders and have excellent flavor due to ample acidity and high sugar content.

The seed resulting from the cross was collected and planted. The resulting plants were then backcrossed using CMS VFN8 as the female parent. The seed resulting from this backcross was collected and planted. The resulting plants were then backcrossed a second time with CMS VFN8 as the female parent. Three additional backcrosses were conducted using the plants resulting from the previous backcross and CMS VFN8 as the female parent. After a total of five backcrosses, the resulting plants, called "CMS VFN8/Det. Parth $1^{*4}$", were homozygous for the pat-2 gene. The CMS VFN8/Det. Parth $1^{*4}$ plants were used as the female parent in a cross to develop the seedless tomato 96 FH 241. Seeds of CMS VFN8/Det. Parth $1^{*4}$ plants have been deposited with the American Type Culture Collection (ATCC), 10801 University Boulevard, Manassas, Va. 20110 on Oct. 13, 1997 and assigned ATCC Deposit Number 209361. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. Seeds of CMS VFN8/Det. Parth $1^{*4}$ plants will be replenished should it become non-viable at the depository.

An open-pollinated tomato variety, called "Delicious", commercially available from Seminis Vegetable Seeds, the assignee of the present invention, was crossed as the female parent with a proprietary tomato plant obtained from Oregon State University, Corvallis, Oreg., called "33" using traditional cross hybridization techniques. 33 contains the parthenocarpic gene pat-2. The seed resulting cross was collected and planted. The resulting plants were backcrossed using Delicious as the female parent. The resulting plants, called "$F_6$('Delicious'/33*)", are homozygous for the pat-2 gene. The $F_6$('Delicious'/33*) plants are used as the male parent in a cross to develop the seedless tomato 96 FH 241. Seeds of the $F_6$('Delicious'/33*) have been deposited with the American Type Culture Collection, 10801 University Boulevard, Manassas, Va. 20110 on Oct. 13, 1997 and assigned ATCC Deposit Number 209360. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. Seeds of $F_6$('Delicious'/33*) plants will be replenished should it become non-viable at the depository.

CMS VFN8/Det. Parth $1^{*4}$ was crossed as the female parent with $F_6$('Delicious'/33*) as the male parent using traditional cross hybridization techniques. The resulting seed was collected and then planted. The resulting tomato, 96 FH 241, was 100% seedless.

Example 2

The sugar content and sugar acid ratios of Shady Lady and 96FH241 were determined. Shady Lady is a commercial variety with a fairly compact determinate vine and generally large fruit size (180–220 g). 96 FH 241 is a seedless hybrid tomato produced by the method of the present invention. Samples from each of these tomatoes were homogenized individually in a standard food blender until a smooth consistency was achieved. Tomato serum from each sample of puree was obtained by centrifuging at 4° C. in a Beckman GS-6R centrifuge at 1000×g for 15 minutes.

The sugar content of the serum was determined using a model RFM91 refractometer (Bellingham & Stanley). The refractometer was calibrated with water and 10°Brix glucose solution. The sugar content is expressed in °Brix (% sugar (wt/wt)). The sugar content for the two tomatoes is shown in the table below.

Titratable acidity (A) was measured using a Mettler D67 autotitrator. An endpoint of pH 8.2 and a D.1000 N sodium hydroxide (VWR) titrant was used. The titratable acidity is expressed in millimoles $H^+$/100 grams serum. The sugar:acid ratio (S/A) is the molar ratio of sugar to titratable $H^+$ content using the following formula: S/A=(°Brix/180.16)/(A/1000). The sugar:acid ratio for the two tomatoes is shown in Table 1 below.

TABLE 1

|  | Brix (sugar) | Sugar:Acid Ratio |
|---|---|---|
| 'Shady Lady' (commercial variety) | 4.47 | 3.71 |
| 96 FH 241 (seedless hybrid) | 6.42 | 3.96 |

The results in the above table demonstrate that the sugar content of a seedless tomato produced by the method of the present invention is higher than a standard, commercial variety of tomato. The sugar:acid ratio of the tomatoes of the present invention are also higher than that of standard tomatoes.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A hybrid *Lycopersicon esculentum* plant which produces fruit which is 100% seedless when the plant is grown in an area having a photoperiod of about twelve hours or greater, wherein said plant is produced by a process comprising the steps of crossing a *Lycopersicon esculentum* plant containing at least one parthenocarpic gene as a male parent with a cytoplasmic male sterile *Lycopersicon esculentum* plant containing at least one parthenocarpic gene as a female parent to produce a hybrid seedless *Lycopersicon esculentum*, wherein at least one parthenocarpic gene in the male parent and at least one parthenocarpic gene in the female parent are identical.

2. The hybrid *Lycoperiscon esculentum* of claim 1, wherein the parthenocarpic gene is selected from the group consisting of: pat, pat-1, pat-2, pat-3, pat-4, pat-5, sha, and sds.

3. A method for making a *Lycopersicon esculentum* plant which produces fruit which is 100% seedless when the plant is grown in an area having a photoperiod of about twelve hours or greater, wherein said plant is produced by the method comprising the steps of crossing a *Lycopersicon esculentum* plant containing at least one parthenocarpic gene as a male parent with a cytoplasmic male sterile *Lycopersicon esculentum* plant containing at least one parthenocarpic gene as a female parent to produce a hybrid seedless *Lycopersicon esculentum*, wherein at least one parthenocarpic gene in the male parent is identical to at least one parthenocarpic gene in the female parent.

4. The method of claim 3, wherein the parthenocarpic gene is selected from the group consisting of: pat, pat-1, pat-2, pat-3, pat-4, pat-5, sha, and sds.

5. A hybrid seedless *Lycopersicon esculentum* fruit produced by the method of claim 3.

\* \* \* \* \*